United States Patent
Tagawa et al.

(10) Patent No.: US 6,475,517 B1
(45) Date of Patent: Nov. 5, 2002

(54) METHOD FOR PREPARING CLOSED VESICLES

(75) Inventors: Toshiaki Tagawa, Kanagawa (JP); Saiko Hosokawa, Kanagawa (JP); Kazuhiro Nagaike, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/897,912

(22) Filed: Jul. 5, 2001

Related U.S. Application Data

(63) Continuation of application No. 08/843,640, filed on Apr. 10, 1997, now abandoned.

(30) Foreign Application Priority Data

Apr. 11, 1996 (JP) ............................................. 8-089277

(51) Int. Cl.[7] ............................................. A61K 9/127
(52) U.S. Cl. ..................................................... 424/450
(58) Field of Search .............................. 424/450, 178.1

(56) References Cited

U.S. PATENT DOCUMENTS

| | | | | |
|---|---|---|---|---|
| 4,247,411 A | * | 1/1981 | Vanlerberghe et al. | 252/316 |
| 4,880,635 A | * | 11/1989 | Janoff et al. | 424/450 |
| 4,927,571 A | * | 5/1990 | Huang et al. | 264/4.3 |
| 5,614,191 A | * | 3/1997 | Puri | 424/178.1 |
| 5,616,341 A | * | 4/1997 | Mayer | 424/450 |
| 5,707,608 A | * | 1/1998 | Liu | 424/9.61 |
| 5,817,334 A | * | 10/1998 | Schmidt et al. | 424/450 |
| 6,221,385 B1 | * | 4/2001 | Camu et al. | 424/450 |

FOREIGN PATENT DOCUMENTS

| | | | |
|---|---|---|---|
| WO | 91/06285 | * | 5/1991 |
| WO | 92/18104 | | 10/1992 |
| WO | 97/04746 | | 2/1997 |

OTHER PUBLICATIONS

Madden et al., Biochimica et Bipophysica Acta, 817, pp. 67–74 (1985).
Van Bommel et al., International Journal of Pharmaceutics, 22, pp. 299–310 (1984).
Madden et al., Liposomes Rational Design, pp. 261–282 (1999).

\* cited by examiner

Primary Examiner—Kenneth R. Horlick
(74) Attorney, Agent, or Firm—Wenderoth, Lind & Ponack, L.L.P.

(57) ABSTRACT

A method for preparing a closed vesicle by a rehydration of a closed vesicle using a rehydration solution, wherein the closed vesicle comprises a dehydrated micelle particle or dehydrated amphipathic micelle bilayers, preferably a liposome loading a pharmaceutically active substance, and the method is characterized in that the rehydration is carried out at a low temperature such as in the range of from 0° C. to 10° C. The method can provide a rehydrated stable vesicle without a leak of the loaded substance.

15 Claims, 2 Drawing Sheets

METHOD FOR PREPARING CLOSED VESICLES

This is a continuation of Ser. No. 08/843,640, filed Apr. 10, 1997, now abandoned.

BACKGROUND OF THE INVENTION

1. Field of the Invention

The present invention relates to a method for preparing closed vesicles which comprises the step of rehydrating closed vesicles composed of dehydrated micelle particles or dehydrated amphipathic micelle bilayers under a specific condition. The present invention also relates to closed vesicles obtained by said method.

2. Background Art

Liposomes are closed vesicles composed of lipid micelle bilayers. They can load fat-soluble substances in the lipid phase and water-soluble substances in the aqueous phase, and can carry macromolecular substances such as proteins as well as low-molecular compounds. They also have high bio-compatibility. For these reasons, various research has been made focusing on their use as carriers of drugs, proteins, nucleic acids and the like for the drug delivery systems (DDS). In recent years, practical research has also progressed particularly on liposomes provided with targeting function through a surface modification of the liposome, in addition to reduction of toxicity and improvement of blood retention time by loading a drug.

However, micelle structures of liposomes are essentially not sufficiently stable from a viewpoint of thermodynamics, and development of methods for long term storage is absolutely necessary for their practical uses.

Japanese Patent Unexamined Publication (KOKAI) No. (Sho) 53-142514/1978 to Evans et al. discloses a "dehydration method" aiming at long-term stability which comprises steps of removing water from a liposome solution to convert into a stable dried lipid state, followed by adding an aqueous solution before use (rehydration) to regenerate liposomes. This method suggested a possibility of long term storage of liposomes in the form of dried powder. Since then, research to achieve improvements has been conducted in order to reduce aggregation, fusion of liposomes, and leaking of loaded substances upon the dehydration.

For example, from viewpoints of protective agents for dehydration, Japanese Patent Publication (KOKOKU) No. (Sho) 61-21449/1986 discloses a method comprising a step of lyophilizing a liposome solution after the addition of hydrophilic compound such as dextran or gum arabic, and Japanese Patent Unexamined Publication for PCT Application (KOHYO) No. (Sho) 62-501631/1987 discloses a method comprising a step of lyophilizing a liposome solution containing a disaccharide such as trehalose or sucrose. In addition, Japanese Patent Unexamined Publication (KOKAI) No. (Hei) 7-145041/1995 discloses liposomes loading an antitumor agent which is dehydrated by a method other than lyophilization process, and Japanese Patent Unexamined Publication (KOKAI) No. (Hei) 7-145043/1995 discloses a method comprising a step of dehydrating a liposome solution without pre-freezing and maintaining a residual water content of 2 to 5%.

Furthermore, from a viewpoint of a solution for the rehydration, Japanese Patent Unexamined Publication (KOKAI) No. (Sho) 53-142514/1978 discloses that lyophilized liposomes were dispersed under warming at a temperature of 50 to 70° C.

However, leaking of loaded substances in a range of about tens to 10% were observed with these methods depending on lipid compositions and the type of loaded substances, and stability of liposomes is sometimes insufficient.

Such leaking of-loaded substance may cause significant disadvantages, in particular, as for liposomes used for assays which can be significantly influenced by a leak of a loaded agent, or liposomes containing a medicament having a potent physiological activity such as an anti-tumor agent or the like. When liposomes loading an anti-tumor agent are clinically applied, even a leak of an amount of 10–30% cannot be a negligible problem because it may affect a reduction of side effects achieved by a liposome formation, or may possibly deteriorate targeting functions.

SUMMARY OF THE INVENTION

The inventors of the present invention conducted research to solve the aforementioned problems of the state of the art. As a result, they found that conditions for the rehydration are unexpectedly important as well as processes having been studied so far, and that the temperature of a dispersion at rehydration is significantly influential. It was found quite surprisingly that the leak of the loaded substances is remarkably suppressed by carrying out the rehydration under cooling, contrary to the conventional warming process for closed vesicles including liposomes, and that closed vesicles rehydrated under a low temperature condition have highly improved stability even after they are warmed up to room temperature. The present invention was achieved on the basis of these findings.

The present invention thus provides a method for preparing a closed vesicle by a rehydration of a closed vesicle comprising a dehydrated micelle particle or dehydrated amphipathic micelle bilayers by using a rehydration solution, characterized in that the rehydration is carried out at a low temperature.

According to preferred embodiments of the present invention, there are provided the aforementioned method wherein the temperature is in the range of from 0° C. to 10° C.; the aforementioned method wherein the closed vesicle is introduced with a pharmaceutically active substance or a diagnostic agent; the aforementioned method wherein the pharmaceutically active substance is an anti-tumor agent; the aforementioned method wherein the anti-tumor agent is selected from the group consisting of adriamycin, daunomycin, vinblastine, and pharmaceutically acceptable salts and derivatives thereof; the aforementioned method wherein the pharmaceutically acceptable salts are formed together with a multivalent anionic substance; the aforementioned method wherein the multivalent anionic substance is selected from the group consisting of citric acid, tartaric acid, and glutamic acid; the aforementioned method wherein the closed vesicle is a liposome; the aforementioned method wherein the liposome is obtained by lyophilizing or spray-drying a liposome containing a saccharide; the aforementioned method wherein the liposome is modified with an antibody and/or polyethylene glycol; and the aforementioned method wherein the rehydration solution has a pH within a neutral area.

According to further aspects of the present invention, there are provided a closed vesicle obtainable by any one of the aforementioned methods; and a pharmaceutical composition containing the above-defined vesicle.

According to still further aspects of the present invention, there are provided a pharmaceutical kit which comprises a dehydrated preparation comprising the dehydrated closed vesicle and a rehydration solution for rehydrating said closed vesicle, characterized in that either or both of the dehydrated preparation and the rehydration solution are used at a low temperature; and a diagnostic kit which comprises a dehydrated preparation comprising the dehydrated closed vesicle and a rehydration solution for rehydrating said closed vesicle, characterized in that either or both of the dehydrated preparation and the rehydration solution are used at a low temperature.

Figure 1:
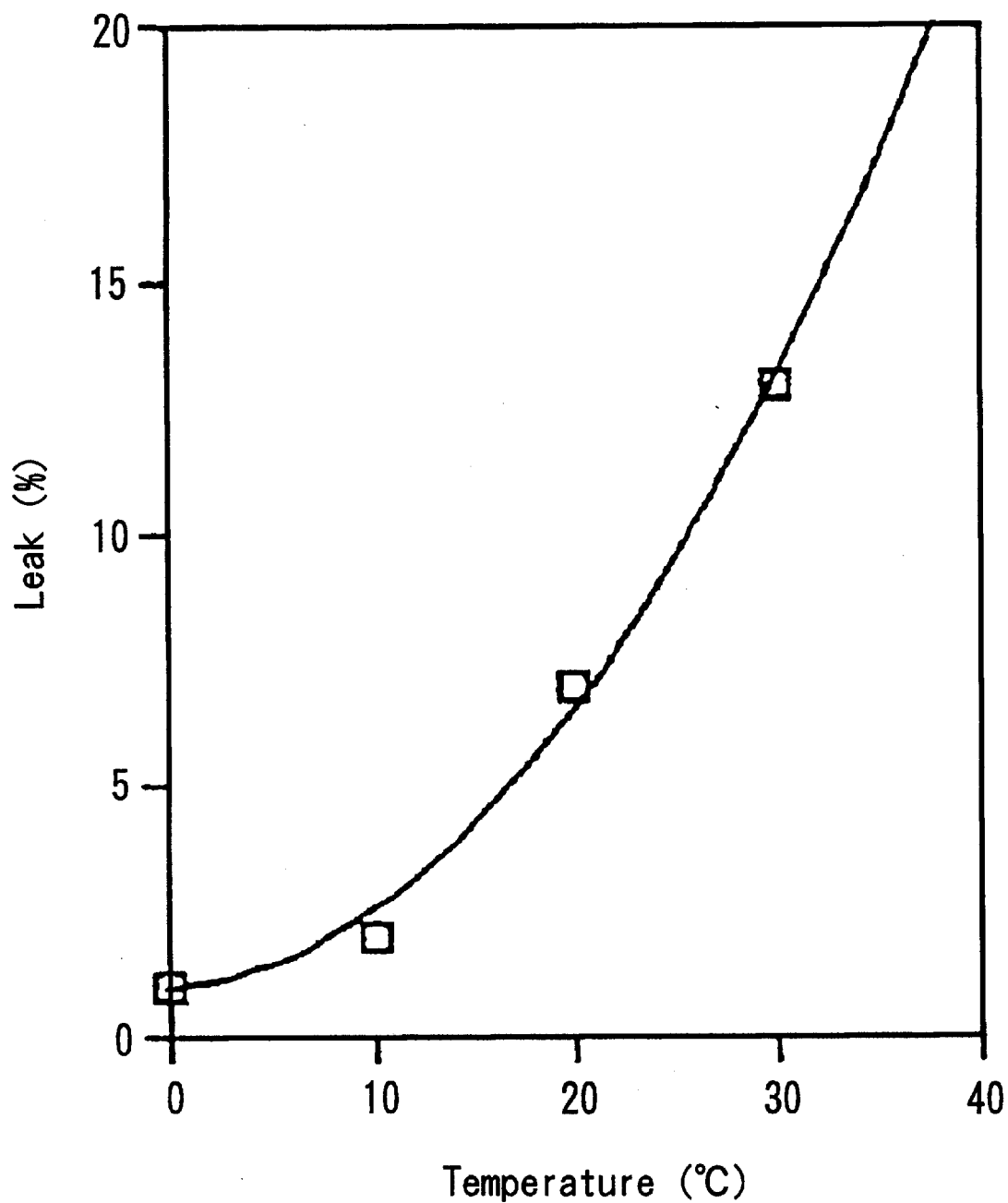
FIG. 1 shows the influence of temperatures of a rehydration solution on the leaks of adriamycin. In the figure, the horizontal axis indicates temperatures of the rehydration solution and the longitudinal axis indicates the leaks of adriamycin.

In the figure, the horizontal axis indicates the amount of liposomes converted into the amount of adriamycin and the longitudinal axis indicates the rates of living cells.

DETAILED EXPLANATION OF THE INVENTION

Preferred Embodiments

In the specification, the term "micelle particles" or "micelles" means water-soluble particles formed by agglomeration of amphipathic molecules each having a hydrophilic moiety and a hydrophobic moiety in a molecule. Such micelle particles or micelles may be present in the forms of small spheres, ellipsoids, or long cylinders, and they may also be in the form of bilayers consisting of two parallel layers of amphipathic molecules as explained below, i.e., amphipathic micelle bilayers.

Also in the specification, the term "closed vesicles" means closed structures consisting of the micelle particles or micelles as mentioned above. Examples include naturally derived closed vesicles such as cells or viruses, and artificial closed vesicles such as liposomes, Novasome (trade name, Micro Vesicular Systems, Inc.) described in Liposome Technology 2nd edition, Vol. 1, p142 (1993), non-ionic surfactant vesicles described in Liposome Technology 2nd edition, Vol. 1, p157 (1993), and polymer microspheres. Among them, liposomes may preferably be used for the present invention.

As the amphipathic molecules forming the micelle particles or the micelles, any molecules may be used so far as the molecule contains a hydrophilic moiety together with a hydrophobic moiety and can form micelle particles or micelles according to a known and ordinarily used process. Among them, lipids are preferable amphipathic molecules.

Examples of the lipids which can constitute the closed vesicles of the present invention include, for example, phospholipids such as naturally derived lecithin (e.g., egg yolk lecithin, soybean lecithin), dipalmitoylphosphatidylcholine (DPPC), dimyristoylphosphatidylcholine (DMPC), distearoylphosphatidylcholine (DSPC), dioleoylphosphatidylcholine (DOPC), dimyristoylphosphatidylethanolamine (DMPE), diparmitoylphosphatidylglycerol (DPPG), and dimyristoylphosphatidic acid (DMPA); glycolipids such as glycosphingolipids and glyceroglycolipids; fatty acids; dialkylmethylammonium amphiphiles, polyglycerol alkylethers, polyoxyethylene alkylethers (Liposome Technology 2nd edition, Vol. 1, p.141, 1993); alkyl glycosides; alkyl methylglucamides; alkyl sucrose esters; dialkyl polyoxyethylene ethers; dialkyl polyglycerol ethers (Liposome Technology 2nd edition, Vol. 1, p.157, 1993); and amphipathic block copolymers such as polyoxyethylene/polylactic acids (Japanese Patent Unexamined Publication for PCT applications (KOHYO) No. (Hei) 6-508831/1994). These lipids may be used alone or in combination of two or more of them, and together with one or more non-polar substances such as cholesterol, if desired.

Where the closed vesicles are liposomes, they may contain charged substances such as stearylamine and dicetyl phosphate; phospholipid derivatives having a water-soluble polymer-moiety such as polyethylene glycol; phospholipid derivatives having maleimide groups or the like. In addition, they may be bound to antibodies or water-soluble polymers through these lipid derivatives as described in, for example, Japanese Patent Unexamined Publication (KOKAI) No. (Hei) 4-346918/1992. They may also be incorporated with a part of or the entire virus such as, for example, a fused liposome which comprises a liposome fused with Sendai virus.

As the closed vesicles, those naturally derived, per se, may be used, or alternatively, those prepared by any methods may also be used. Where the closed vesicles are liposomes, for example, they can be prepared by using the aforementioned materials according to known and ordinarily used manufacturing processes. Examples of applicable liposomes include multilamellar liposomes (MLV) prepared by the addition of an aqueous solution to a lipid film formed on the surface of a glass wall and followed by mechanical shaking; small unilamellar liposomes (SUV) obtained by the ultrasonic irradiation process, the ethanol injection method, the French press method or the like; large unilamellar liposomes (LUV) obtained by the detergent dialysis method, the reverse phase evaporation method (Liposome, J. Sunamoto et al., Nankodo, 1988), and the extrusion method in which MLV are extruded through a membrane having a uniform pore size under a raised pressure (Liposome Technology, Vol. 1, 2nd Edition).

Examples of the pharmaceutically active substances which can be introduced into the closed vesicles include anti-tumor agents such as adriamycin, daunomycin, vinblastine, cisplatin, and 5-FU (fluorouracil); adrenergic blockers such as timolol; antihypertensive agents such as clonidine; antiemetics such as procainamide; antimalarics such as chloroquine; pharmaceutically acceptable salts or derivatives thereof; toxic proteins such as lysin A and diphtheria toxin and DNAs encoding such proteins; and DNAs encoding cytokines such as TNF and the like.

As the pharmaceutically acceptable salts of the antitumor agents and the like as mentioned above, preferable salts include, for example, pharmaceutically acceptable multivalent ionic substances such as citric acid, tartaric acid, glutamic acid, and derivative thereof. Among these pharmaceutically active substances which can be incorporated into the closed vesicles, antitumor agents are preferred.

Examples of the diagnostic agents which can be introduced into the closed vesicle include, for example, imaging agents containing radioisotopes such as indium or technetium; contrasting agents containing iodine or gadolinium; enzymes such as horse radish peroxidase, alkaline phosphatase, or β-galactosidase; fluorescent substances such as europium derivatives; luminescent substances such as N-methylacrydium derivatives or the like.

These pharmaceutically active substances or diagnostic agents may be introduced into the closed vesicles according to ordinarily used processes known per se. For example, where the closed vesicle are liposomes, the substances as aqueous solutions may be added at the time of preparing liposomes and loaded, or processes may be applied in which ionizable drugs are taken into liposomes by potential energy as driving force that is generated by the formation of concentration gradient such as a pH gradient between the inside and outside of the vesicles (Cancer Res. 49, p.5922, 1989; and BBA, 455, p.269, 1976).

For the dehydration of the closed vesicles, known methods such as lyophilization and spray drying may be applied. Preferably, lyophilization is applied. Saccharides such as sucrose or trehalose may be added as lyophilization aids. The saccharide may be added at least in the external liquid phase during the dehydration of liposomes. The concentration of the saccharide which can be added in the external liquid phase may generally be from 5 to 40%, preferably from 5 to 20%.

As the rehydration solution, aqueous solutions containing salts such as physiological saline, neutral buffers such as phosphate buffers, saccharide solutions such as those containing tit glucose, or mixtures thereof may be used. The pH of the rehydration solution may preferably be in a neutral area such as in the range of from 6 to 8, more preferably from 6.5 to 7.5. pH adjusting buffers may be added in any manner so far as the aqueous solutions containing the closed vesicles have pHs in the neutral area during the rehydration process. For example, they may be added in the rehydration solutions, or alternatively, they may be added in liposomes at the time of lyophilization of the liposomes, or may be contained in both of the rehydration solution and lyophilized liposomes. The concentration of the pH adjusting buffer may generally be from 1 to 100 mM, preferably 5 to 50 mM.

Each of the closed vesicles and the rehydration solution, preferably the closed vesicles in the form of a suspension in a suitable aqueous medium and the rehydration solution, is subjected to sterilization by filtration, and then filled into a pharmaceutical container such as a suitable vial, ampoule or the like under sterile condition. The rehydration solution may be sealed without further treatment, and the closed vesicles are sealed after dehydration, e.g., lyophilization.

The rehydration can be carried out by dispersing the dehydrated closed vesicles in the rehydration solution under low temperature conditions. The low temperature condition herein used means a temperature below room temperature, usually a temperature of about 20° C. or lower, i.e., a temperature ranging from about 20° C. down to a temperature at which the rehydration solution does not freeze and can exist in the state of a solution. The temperature range between about 10° C. to 0° C. is preferred.

The low temperature condition for the rehydration may be applied by any method so long as a temperature in the aforementioned range can be achieved. For example, either or both of the pharmaceutical container, e.g., a vial, containing the dehydrated closed vesicles, and the rehydration solution, may be cooled beforehand at a low temperature, or alternatively, the dehydrated closed vesicles may be dispersed in the rehydration solution while cooling under the low temperature condition using a suitable refrigerant during the rehydration process.

Period of time for the rehydration is not particularly limited so long as it can achieve uniform dispersion of the closed vesicles in the rehydration solution. The period may vary depending on the size of a vessel, agitation rate and the like, and is generally about 1 minute or less. By maintaining the aforementioned low temperature condition during said period, a reduced leaking of the loaded substance is achievable and the dehydrated closed vesicles can be stably rehydrated.

A composition containing the closed vesicles obtained by rehydration as mentioned above, e.g., a pharmaceutical composition containing liposomes that encapsulate a pharmaceutically active substance, can be used through intravascular, intravesical, intraperitoneal, or topical administration for the treatment of various diseases such as cancers. Administration dose may appropriately chosen depending on the sort of loaded active substance. For example, as for vesicles loading adriamycin, a dose may be not more than 10 mg/kg, preferably not more than 5 mg/kg, more preferably not more than 1 mg/kg of adriamycin.

The present invention also encompasses a pharmaceutical or diagnostic kit composed of two unit components, i.e., a dried preparation containing the dehydrated closed vesicles loading a pharmaceutically active substance or a diagnostic agent and the rehydration solution for rehydrating the closed vesicles. The invention also encompasses a pharmaceutical or diagnostic kit composed of three unit components, i.e a lyophilized preparation containing a pharmaceutically active substance or a diagnostic agent and a dried preparation containing the dehydrated closed vesicles each of which is filled in a separate container, together with the rehydration solution. Where the three component kit is used, the dehydrated preparation containing the dehydrated closed vesicles is rehydrated under the low temperature condition in the manner described above, and then the pharmaceutical preparation or the diagnostic preparation dissolved in a suitable solvent beforehand is added to the rehydrated closed vesicle solution. By these processes, the pharmaceutically active substance or the diagnostic agent can be taken into the closed vesicles by a potential energy generated between the inside and outside of the vesicles as explained above.

EXAMPLES

The present invention will be further explained in detail by referring to the following examples. However, the scope of the present invention is not limited to these examples.

Example 1

Dipalmitoylphosphatidylcholine (DPPC), cholesterol (chol), and ε-maleimidecaproyldipalmitoylphosphatidylethanolamine were dissolved in chloroform in a molar ratio of 18/10/0.5, and then dried under reduced pressure using a rotary evaporator. The residue was dried under reduced pressure using a vacuum pump to remove the remaining solvent. 0.3 M citric acid buffer (pH 4.0) was added to the resulting lipid film in the ratio of 1 ml of the buffer per 100 mg of the film. The mixture was warmed up to 60° C. and emulsified by shaking using a vortex mixer to form MLV liposomes. The liposomes (MLV) were subjected to a sizing treatment by the extruder method. The liposomes were passed through a 0.2 µm nucleopore membrane equipped by an extruder (Nichiyu Liposome Co., Ltd.) and successively through a 0.1 µm nucleopore membrane to form LUV liposomes. The aqueous phase outside the liposomes was neutralized with 1N sodium hydroxide solution, and the mixture was added with a 20 mg/ml aqueous solution of adriamycin (ADM) in a ratio of 10 mg of AD)M per 100 mg of the lipid under warming at 60° C. More than 95% of the ADM was loaded into the liposomes by pH gradient between the inside and outside of the liposomes. The ADM not loaded was removed by gel filtration, and the solution outside the liposomes was adjusted to 10% sucrose concentration and then the mixture was lyophilized to give dehydrated liposomes.

50 mM phosphate buffer (pH 7.5) cooled under ice bath was added to the lyophilized liposomes so that the volume before the lyophilization was recovered and then rehydration was performed by shaking the vial (temperature during the rehydration was 0° C.).

A part of the mixture was subjected to a gel filtration using a column of NAP-10 (Pharmacia) equilibrated with phosphate-buffered saline (PBS) to separate ADM loaded in the liposomes from leaked ADM.

The amount of ADM maintained in the liposomes was measured through observation of absorbance at 500 nm after the addition of 0.3 M hydrochloric acid/50% ethanol and extraction at 60° C. The leaked ADM was quantified through the observation of absorbance at 500 nm of the solution without further treatment. As a result, the rate of leak was not more than 3%, which was similar to that observed for liposomes treated with a simple freeze-thawing process. No agglomeration of liposomes was observed.

Comparative Example 1

Liposomes were prepared and rehydrated in the same manner as in Example 1 except that the rehydration solution was replaced with distilled water at room temperature (25° C.). Although no agglomeration or the like was observed, approximately 15% to 25% of ADM was leaked.

Example 2

Antibodies having thiol groups were prepared according to the method described in Biochemistry, 12, p.3206, 1973 by reacting iminothiolane with GAH antibodies described in EP 520 499 (monoclonal antibodies reactive to gastric carcinoma). Polyethylene glycol (PEG) having thiol groups was also prepared by reacting 2,4-bis(polyethylene glycol)-6-chloro-s-triazine with cystine and then reducing the reaction product.

Liposomes prepared in the same manner as in Example 1 were reacted with the thiol-introduced antibodies and the thiolated PEG groups successively to give liposomes modified with the antibodies and PEG. The outer liquid phase was replaced with 10% sucrose, and lyophilization was performed. The lyophilized liposomes were added with 50 mM phosphate buffer (pH 7.5) adjusted at 0° C. to 30° C. and dispersed, and then the amount of ADM leaked was measured in the same manner as those described above. As a result, the increase of the leak was observed depending on the temperature of the rehydration solution as shown in FIG. 1.

Example 3

Lyophilized liposomes prepared in the same manner as those in Example 2 were added with 50 mM phosphate buffer (pH 7.5) chilled at 0° C. and dispersed. The dispersion was then applied to a gel filtration column (NAP-10, Pharmacia) to remove ADM leaked during the rehydration process. The liposome fraction was warmed over a water bath at 37° C. and newly leaked ADM was measured. As a result, substantially the entire amount of the ADM was retained in the liposomes, and thus the liposomes once rehydrated at low temperature was stable even after warming.

Comparative Example 2

Leak after the rehydration was measured in the same manner as those in Example 3 except that the rehydration solution was replaced with physiological saline adjusted at room temperature (25° C.). Additional ADM leak of about 6% was observed after warming at 37° C. for 1 hour.

Example 4

Antitumor activity of the liposomes of Example 2 which loaded ADM and were bound to anti-tumor antibodies and PEG was examined in vitro using gastric carcinoma cell line B37 (reactive to the GAH antibodies used in Example 2) established from human gastric carcinoma tissue.

The cells were inoculated to a 96-well culture plate. After the cells had adhered to the plate next day, the cells were added with liposomes which were stored at −20° C. for 5 months after dehydration (lyophilization) and then rehydrated with 50 mM phosphate buffer (pH 7.5) at a low temperature (0° C.), or added with liposomes which were thawed after having been stored in frozen state with 10% sucrose for 5 months. After reaction at 37° C. for 1 hour, the liposomes were removed and the cells were added with 10% serum culture medium, and cultivation was continued. After 5 days, the rate of living cells was measured by the MTT method (J. Immunol. Methods, 65, 55, 1983) for comparison of the activity.

Figure 2:
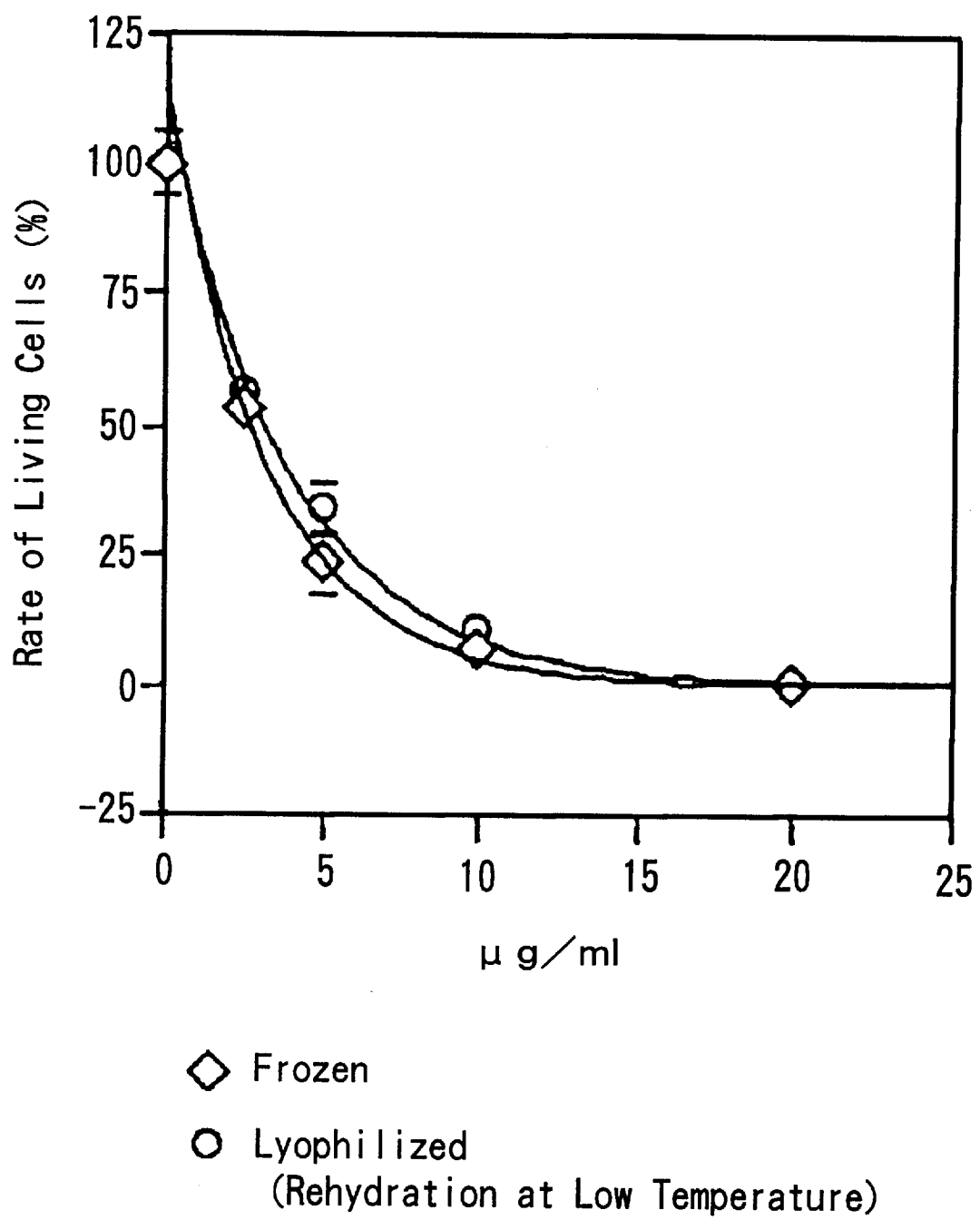
FIG. 2 shows anti-tumor activities of liposomes subjected to lyophilization and rehydration at a low temperature and cryo-preserved liposome.

As a result, the liposomes lyophilized/rehydrated at a low temperature maintained the same level of anti-tumor activity as that of the cryopreserved liposomes as shown in FIG. 2.

According to the present invention, leaking of a loaded substance which is accompanied with a regeneration process of closed vesicles from dedydrated liposomes can be remarkably reduced, and closed vesicles are obtainable which are stable after a rehydration process.

What is claimed is:

1. A method for reducing leakage of loaded substance in the form of a solution, encapsulated in a closed vesicle, which method comprises dehydrating loaded micelle particles or loaded amphipathic micelle bilayers to form dehydrated micelle particles or dehydrated amphipathic micelle bilayers and then rehydrating said dehydrated micelle particles or amphipathic micelle bilayers by using a rehydration solution, wherein said rehydration is carried out in the presence of a saccharide in an outer aqueous phase of said closed vesicle at a temperature of about 20° C. or lower, and said closed vesicle before being rehydrated containing no internal saccharide therein, to reduce leakage of the loaded substance.

2. The method according to claim 1 wherein said saccharide is sucrose.

3. The method according to claim 1, wherein the temperature is in the range of from 0° C. to 10° C.

4. The method according to claim 1, wherein the closed vesicle is introduced with a pharmaceutically active substance or a diagnostic agent as the loaded substance.

5. The method according to claim 4, wherein the pharmaceutically active substance is an anti-tumor agent.

6. The method according to claim 5, wherein the anti-tumor agent is selected from the group consisting of adriamycin, daunomycin, vinblastine, a pharmaceutically acceptable salt thereof and derivatives thereof.

7. The method according to claim 6, wherein the pharmaceutically acceptable salt is formed together with a multivalent anionic substance.

8. The method according to claim 7, wherein the multivalent anionic substance is selected from the group consisting of citric acid, tartaric acid, and glutamic acid.

9. The method according to claim 1, wherein the closed vesicle is a liposome.

10. The method according to claim 9, wherein the liposome is obtained by lyophilizing or spray-drying a liposome in a liquid containing a saccharide.

11. The method according to claim 9, wherein the liposome is modified with an antibody and/or polyethylene glycol.

12. The method according to claim 1, wherein the rehydration solution has a pH within the neutral area.

13. The method according to claim 1, wherein the loaded substance is a water-soluble substance in an aqueous phase.

14. The method according to claim 1 wherein a saccharide is contained only in a liquid phase external to said micelle particles or amphipathic micelle bilayers during said dehydration.

15. The method according to claim 6 wherein the anti-tumor agent is adramycin.

* * * * *